US008700425B2

(12) United States Patent
Hitney et al.

(10) Patent No.: US 8,700,425 B2
(45) Date of Patent: Apr. 15, 2014

(54) DYNAMICALLY PREDICTING PATIENT INFLUX INTO AN EMERGENCY DEPARTMENT

(75) Inventors: Raymond R. Hitney, Buchanan, NY (US); Martin S. Kohn, East Hills, NY (US); Erik T. Mueller, Chevy Chase, MD (US)

(73) Assignee: International Business Machines Corporation, Armonk, NY (US)

( * ) Notice: Subject to any disclaimer, the term of this patent is extended or adjusted under 35 U.S.C. 154(b) by 588 days.

(21) Appl. No.: 12/795,106

(22) Filed: Jun. 7, 2010

(65) Prior Publication Data
US 2011/0301965 A1    Dec. 8, 2011

(51) Int. Cl.
*G06Q 10/00*    (2012.01)
*G06Q 50/00*    (2012.01)

(52) U.S. Cl.
USPC .................................................. 705/2; 705/3

(58) Field of Classification Search
USPC ........................................................ 705/2, 3
See application file for complete search history.

(56) References Cited

U.S. PATENT DOCUMENTS

| 6,064,986 | A | 5/2000 | Edelman | |
|---|---|---|---|---|
| 6,154,731 | A | 11/2000 | Monks et al. | |
| 7,480,629 | B2 | 1/2009 | Dashefsky et al. | |
| 7,657,442 | B2 | 2/2010 | Merkin | |
| 2002/0107769 | A1* | 8/2002 | Dashefsky et al. | 705/35 |
| 2005/0209886 | A1 | 9/2005 | Corkern | |
| 2007/0226008 | A1* | 9/2007 | Halsted et al. | 705/2 |
| 2009/0315735 | A1 | 12/2009 | Bhavani et al. | |

OTHER PUBLICATIONS

A. Wiinamaki et al., "Using Simulation in the Architecture Concept Phase of an Emergency Department Design", Proceedings of the 2003 Winter Simulation Conference, pp. 1912-1916, 2003.
H. Xie et al., "A Semi-Open Queueing Network Approach to the Analysis of Patient Flow in Healthcare Systems", 20TH IEEE International Symposium on Computer-Based Medical Systems, pp. 719-724, IEEE Computer Society, Los Alamitos, CA, USA, June 2007.
C. Jurishica, "Emergency Department Simulations: Medicine for Building Effective Models", Proceedings of the 2005 Winter Simulation Conference, pp. 2674-2680, 2005.
Jmh Vissers, "Patient Flow-Based Allocation of Inpatient Resources: A Case Study", European Journal of Operational Research, vol. 105, No. 2, 356-370, March 1, 1998.
A. Tay, "Assessing Competition in Hospital Care Markets: The Importance of Accounting for Quality Differentiation", Rand Journal of Economics, vol. 34, No. 4, 7860814, Winter 2003.

(Continued)

*Primary Examiner* — Luke Gilligan
*Assistant Examiner* — Maroun Kanaan
(74) *Attorney, Agent, or Firm* — John R. Pivnichny; Law Office of Jim Boice

(57) ABSTRACT

Current patients in an emergency department of a hospital are described according to their quantity, their triage classification levels, and their wait times to calculate a current patient backlog. A sum of weight-adjusted triage classification levels of all of the current patients is calculated. Current patient arrival rates in the emergency department are tracked to calculate a current change in patient arrival rates, which are compared with historical changes in patient arrival rates. A size of an imminent influx of arriving patients into the emergency department is then predicted based on the current patient backlog, the sum of weight-adjusted triage classification levels of patients currently in the emergency department, and the current change in patient arrival rates.

18 Claims, 3 Drawing Sheets

(56) References Cited

OTHER PUBLICATIONS

B. Morrison et al., "A Methodology for Modeling Front Office and Patient Care Processes in Ambulatory Health Care", Proceedings of the 2003 Winter Simulation Conference, pp. 1882-1886, 2003.

G. Stiglic et al., "Intelligent Patient and Nurse Scheduling in Ambulatory Health Care Centers", 2005 27th Annual International Conference of the IEEE Engineering in Medicine in Biology Society, 2006.

* cited by examiner

DYNAMICALLY PREDICTING PATIENT INFLUX INTO AN EMERGENCY DEPARTMENT

BACKGROUND

The present disclosure relates to the field of computers, and specifically to the use of computers with patient flow. Still more particularly, the present disclosure relates to the use of computers to dynamically predict future patient flow into an emergency department of a hospital.

BRIEF SUMMARY

A computer implemented method, system and/or computer program product dynamically predict a size of an imminent influx of arriving patients to an emergency department of a hospital. Current patients in the emergency department are described according to their quantity, their triage classification levels, and their wait times to calculate a current patient backlog. A sum of weight-adjusted triage classification levels of all of the current patients is calculated. Current patient arrival rates in the emergency department are tracked to calculate a current change in patient arrival rates, which are compared with historical changes in patient arrival rates. Previous impacts on hospital resources that correspond to the historical changes to patient arrival rates are retrieved to create a predicted current impact on hospital resources. A size of an imminent influx of arriving patients into the emergency department is then predicted based on the current patient backlog, the sum of weight-adjusted triage classification levels of patients currently in the emergency department, the current change in patient arrival rates, and the predicted current impact on hospital resources.

DETAILED DESCRIPTION

Figure 1:
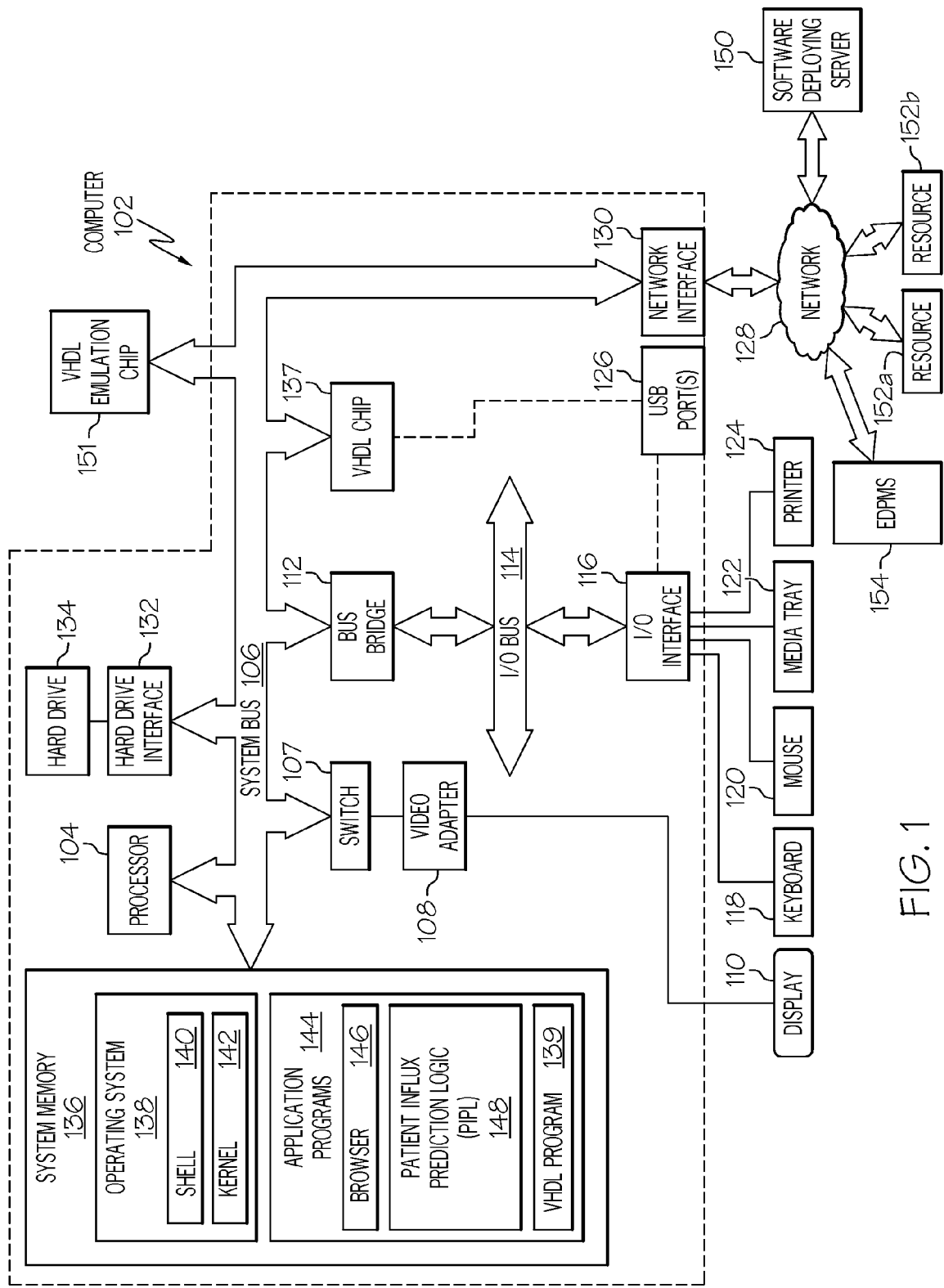
FIG. 1 depicts an exemplary computer in which the present disclosure may be implemented.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including, but not limited to, wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

With reference now to the figures, and in particular to FIG. 1, there is depicted a block diagram of an exemplary computer 102, which may be utilized by the present invention. Note that some or all of the exemplary architecture, including both depicted hardware and software, shown for and within computer 102 may be utilized by software deploying server 150, resources 152a-b (where "b" is an integer") and/or emergency department patient monitoring system (EDPMS) 154.

Computer 102 includes a processor 104 that is coupled to a system bus 106. Processor 104 may utilize one or more processors, each of which has one or more processor cores. A video adapter 108, which drives/supports a display 110, is also coupled to system bus 106. In one embodiment, a switch 107 couples the video adapter 108 to the system bus 106. Alternatively, the switch 107 may couple the video adapter 108 to the display 110. In either embodiment, the switch 107 is a switch, which may be mechanical, that allows the display 110 to be coupled to the system bus 106, and thus to be functional only upon execution of instructions (e.g., patient influx prediction logic—PIPL 148 described below) that support the processes described herein.

System bus 106 is coupled via a bus bridge 112 to an input/output (I/O) bus 114. An I/O interface 116 is coupled to I/O bus 114. I/O interface 116 affords communication with various I/O devices, including a keyboard 118, a mouse 120, a media tray 122 (which may include storage devices such as CD-ROM drives, multi-media interfaces, etc.), a printer 124, and (if a VHDL chip 137 is not utilized in a manner described below), external USB port(s) 126. While the format of the ports connected to I/O interface 116 may be any known to those skilled in the art of computer architecture, in one embodiment some or all of these ports are universal serial bus (USB) ports.

As depicted, computer 102 is able to communicate with a software deploying server 150 using a network interface 130. Network 128 may be an external network such as the Internet, or an internal network such as an Ethernet or a virtual private network (VPN).

A hard drive interface 132 is also coupled to system bus 106. Hard drive interface 132 interfaces with a hard drive 134. In one embodiment, hard drive 134 populates a system memory 136, which is also coupled to system bus 106. System memory is defined as a lowest level of volatile memory in computer 102. This volatile memory includes additional higher levels of volatile memory (not shown), including, but not limited to, cache memory, registers and buffers. Data that populates system memory 136 includes computer 102's operating system (OS) 138 and application programs 144.

OS 138 includes a shell 140, for providing transparent user access to resources such as application programs 144. Generally, shell 140 is a program that provides an interpreter and an interface between the user and the operating system. More specifically, shell 140 executes commands that are entered into a command line user interface or from a file. Thus, shell 140, also called a command processor, is generally the highest level of the operating system software hierarchy and serves as a command interpreter. The shell provides a system prompt, interprets commands entered by keyboard, mouse, or other user input media, and sends the interpreted command(s) to the appropriate lower levels of the operating system (e.g., a kernel 142) for processing. Note that while shell 140 is a text-based, line-oriented user interface, the present invention will equally well support other user interface modes, such as graphical, voice, gestural, etc.

As depicted, OS 138 also includes kernel 142, which includes lower levels of functionality for OS 138, including providing essential services required by other parts of OS 138 and application programs 144, including memory management, process and task management, disk management, and mouse and keyboard management.

Application programs 144 include a renderer, shown in exemplary manner as a browser 146. Browser 146 includes program modules and instructions enabling a world wide web (WWW) client (i.e., computer 102) to send and receive network messages to the Internet using hypertext transfer protocol (HTTP) messaging, thus enabling communication with software deploying server 150 and other described computer systems.

Application programs 144 in computer 102's system memory (as well as software deploying server 150's system memory) also include a patient influx prediction logic (PIPL) 148. PIPL 148 includes code for implementing the processes described below, including those described in FIGS. 2-3. In one embodiment, computer 102 is able to download PIPL 148 from software deploying server 150, including in an on-demand basis, wherein the code in PIPL 148 is not downloaded until needed for execution to define and/or implement the improved enterprise architecture described herein. Note further that, in one embodiment of the present invention, software deploying server 150 performs all of the functions associated with the present invention (including execution of PIPL 148), thus freeing computer 102 from having to use its own internal computing resources to execute PIPL 148.

Also stored in system memory 136 is a VHDL (VHSIC hardware description language) program 139. VHDL is an exemplary design-entry language for field programmable gate arrays (FPGAs), application specific integrated circuits (ASICs), and other similar electronic devices. In one embodiment, execution of instructions from PIPL 148 causes VHDL program 139 to configure VHDL chip 137, which may be an FPGA, ASIC, etc.

In another embodiment of the present invention, execution of instructions from PIPL 148 results in a utilization of VHDL program 139 to program a VHDL emulation chip 151. VHDL emulation chip 151 may incorporate a similar architecture as described above for VHDL chip 137. Once PIPL 148 and VHDL program 139 program VHDL emulation chip 151, VHDL emulation chip 151 performs, as hardware, some or all functions described by one or more executions of some or all of the instructions found in PIPL 148. That is, the VHDL emulation chip 151 is a hardware emulation of some or all of the software instructions found in PIPL 148. In one embodiment, VHDL emulation chip 151 is a programmable read only memory (PROM) that, once burned in accordance with instructions from PIPL 148 and VHDL program 139, is permanently transformed into a new circuitry that performs the functions needed to perform the process described below in FIGS. 2-3.

The hardware elements depicted in computer 102 are not intended to be exhaustive, but rather are representative to highlight essential components required by the present invention. For instance, computer 102 may include alternate memory storage devices such as magnetic cassettes, digital versatile disks (DVDs), Bernoulli cartridges, and the like. These and other variations are intended to be within the spirit and scope of the present invention.

Figure 2:
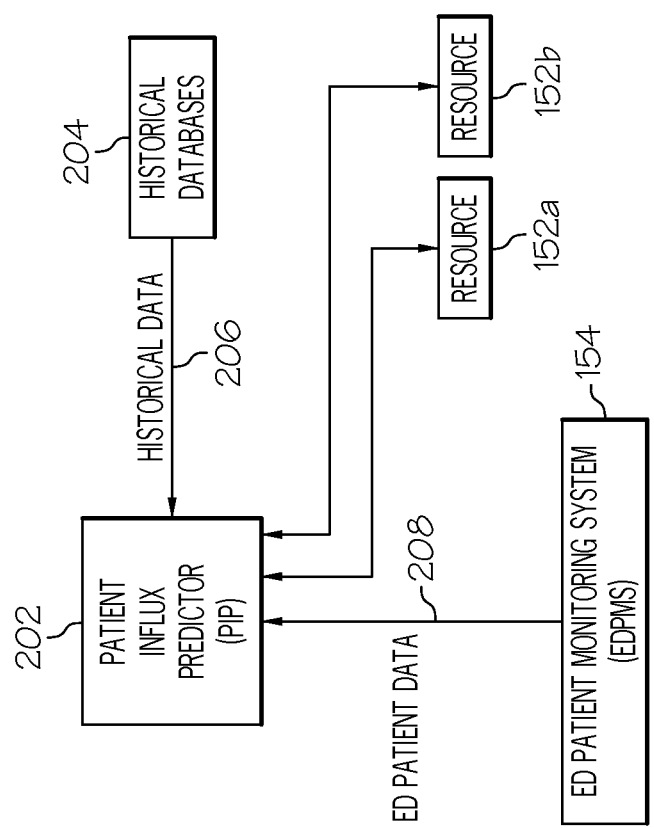
FIG. 2 illustrates relationships among a patient influx predictor (PIP), resources, and an emergency department patient monitoring system (EDPMS)

Referring now to FIG. 2, a patient influx predictor (PIP) 202, which is analogous to computer 102 shown in FIG. 1, is coupled to historical databases 204 (i.e., contents of hard drive 134 and/or media tray 122 shown in FIG. 1), resources 152a-b, and an emergency department patient monitoring system (EDPMS) 154, also shown in FIG. 1. Resources 152a-b may be any resource needed by a patient in an emergency department (ED), also called an emergency room (ER). The ED is a department of a hospital in which emergency patients arrive via ambulance, personal vehicles, or by walking in order to receive emergency medical treatment for acute medical maladies or injuries. Resources 152a-b include, but are not limited to, an open bed in the ED, an open bed outside the ED but within the same or a different hospital, radiology equipment, radiology technicians, medical laboratory equipment, medical laboratory technicians, nurses, and physicians. Part of resources 152a-b is logic and transmission means (e.g., processor 104, PIPL 148 and network interface 130 shown in FIG. 1 as exemplary components of resources 152a-b) for communicating the descriptions of how resources 152a-b have been utilized in the past during past historical changes in patient influx levels. For example, if the resource is hardware such as a computer tomography (CT) machine, logic (e.g., computer 102) associated with that CT machine is able to communicate to TAC 202 how much that CT machine was used when the patient load in the ED reached a certain level or had a specific increase or decrease in the rate at which patients were arriving at the ED. If a resource (e.g., one or more of resources 152a-b) is purely a health care provider, such as a nurse or doctor, then logic (e.g., computer 102) associated with that personnel resource may be a scheduling computer, a tracking system used to identify where the needed worker was located within the hospital, etc. when the patient load in the ED varied in the past. In one embodiment, this data is historical data 206 that is stored in and retrieved from historical databases 204, which may be part of PIP 202, part of computers associated with the resources 152a-b, or from any other storage device/computer.

EDPMS 154 is a tracking system that monitors patients within the emergency department (ED) in real time. EDPMS 154 is also aware of, and in one embodiment is used to calculate, ED patient data 208, which includes the number of patients in the ED, any changes in arrival rates of patients arriving at the ED for treatment, ED patient triage classification levels, maximum and average wait times for ED patients according to their triage classification levels, etc. While EDPMS 154 can utilize any triage system, in one embodiment EDPMS 154 utilizes the Emergency Severity Index (ESI) system. Under the ESI system, Level 1 patients are those that require immediate life-saving intervention. Level 2 patients are those that are at high risk, or are confused and disoriented, or are in severe pain. Typically, Level 2 patients should be seen within 30 minutes. Levels 3-5 are for patients who do not require immediate attention. Level 5 patients require no services/resources outside of the ED (i.e., they do not require any lab work, x-rays, etc.). Level 4 patients require one service/resource outside of the ED. Level 3 patients require multiple services/resources outside of the ED. Note that a Level 3 patient can be moved up to Level 2 if vital signs (heart rate, blood pressure, oxygen saturation) go into a danger zone, even if the patients do not meet the usual requirements to be classified as a Level 2 patient.

Figure 3:
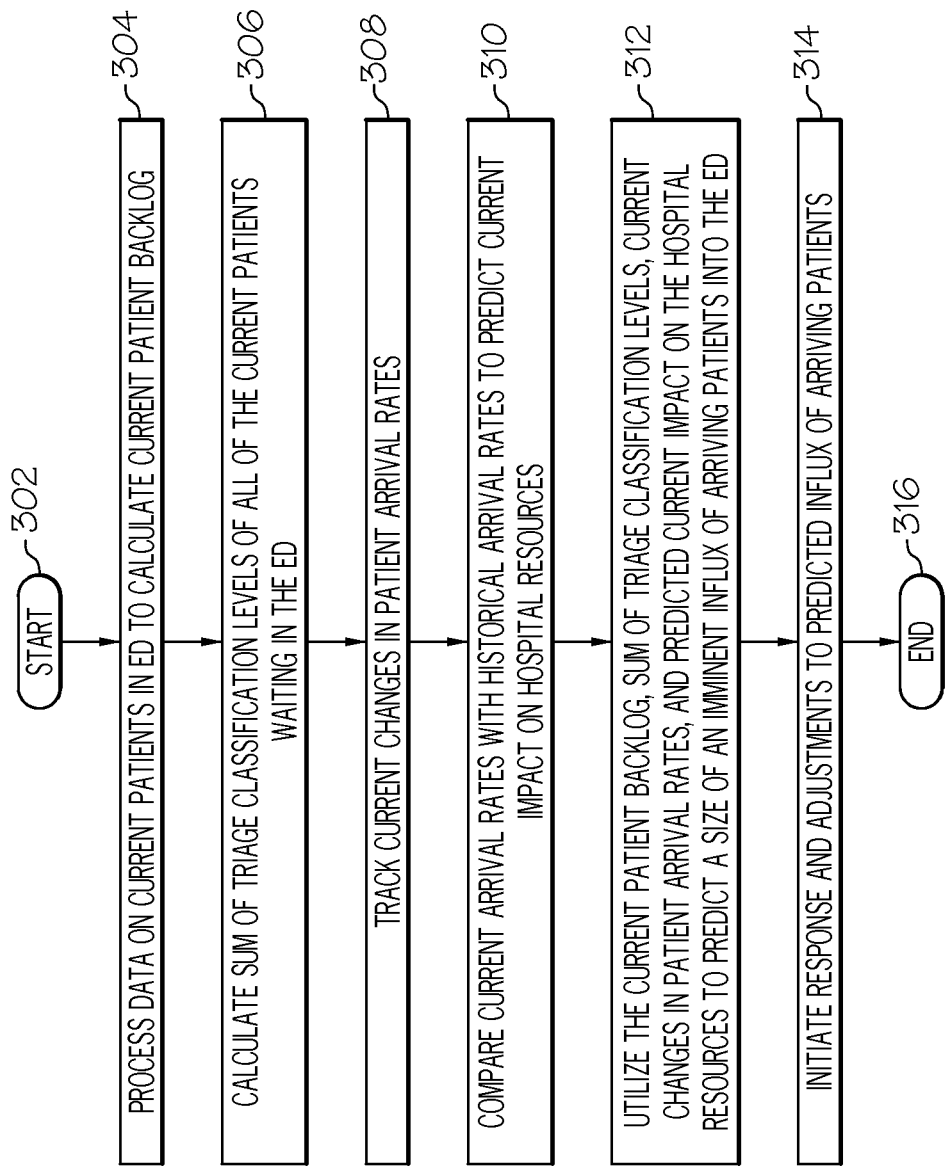
FIG. 3 is a high level flow chart of one or more exemplary steps taken by a processor to dynamically predict a size of an imminent influx of arriving patients into an ED of a hospital.

In a manner described in detail herein, PIP 202 utilizes historical data 206 and ED patient data 208 predict a future rate of influx of new patients arriving at the ED. Referring now to FIG. 3, a high level flow chart of one or more exemplary steps taken by a processor to dynamically predict a size of an imminent influx of arriving patients into an ED of a hospital is presented. After initiator block 302, data related to current patients in the ED is received and processed to calculate a current patient backlog in the ED (block 304). In one embodiment, this is performed by a processor (e.g., part of PIP 202 shown in FIG. 2) receiving an input that describes a quantity of current patients in each triage classification level. Each patient is currently waiting in the ED on a current date, and each patient has been assigned a triage classification level/number. The processor determines a longest wait time in the ED that is experienced by a current patient from each triage classification level. The processor also determines an average wait time that patients, from each triage classification level, are currently waiting in the ED. Finally, the processor calculates a current patient backlog in the emergency department based on the quantity of current patients, the longest wait time for each triage classification level and the average wait time for each triage classification level.

As described in block 306, the processor then calculates a sum of weight-adjusted triage classification levels of all of the current patients waiting in the ED. For example, assume that there are currently ten patients waiting in the ED. One patient has a triage classification level of 1, three patients are rated at 2, and six patients are rated at 5. However, in order to reflect the true level of criticality, the normal triage figures (1-5) are inverted (5-1), such that the most critical patient is now given a value of 5, while the least critical is given a value of 1. Thus, in the example given, the one patient has a weight-adjusted triage classification level of 5, the three patients have a weight-adjusted triage classification level of 4, and the six patients have a weight-adjusted triage classification level of 1. Thus, the sum of the weight adjusted triage classification levels is 23 ((1*5)+(3*4)+(6*1)). Using this weighted system, a larger sum of triage classification levels of all patients currently in the ED predicts a relatively higher imminent influx of arriving patients into the ED, and a smaller sum of triage classification levels of all patients currently in the ED predicts a relatively lower imminent influx of arriving patients into the ED.

As described in block 308, the processor tracks current patient arrival rates in the ED to calculate a current change in patient arrival rates. For example, if patients were arriving at the ED at the rate of 10 an hour during the previous hour, but are now arriving at the ED at the rate of 20 an hour during the current hour, then the patient influx increase rate is acknowledged and stored by the processor.

As depicted in block 310, the processor compares the current change in patient arrival rates (determined in block 308) to historical changes in patient arrival rates to predict a current impact on hospital resources. These historical changes in patient arrival rates are from one or more prior dates that share a common feature with the current date. Examples of such common features include, but are not limited to, the current date and the prior dates falling on a same holiday; the current date and the prior dates falling on a same day of the week; the current date and the prior dates falling on a same calendar date; data from the current date and the prior dates coming from a same time of day (i.e., 8:00-9:00 PM). The processor can determine a previous impact on hospital resources by patients from the ED. That is, the processor can correlate what impact the historical changes to patient arrival rates (from prior dates) had on hospital resources. From this correlation, the processor creates a predicted current impact on hospital resources. This predicted current impact is for predicted use of the hospital resources by the current patients. If the current impact on hospital resources (i.e., what resources are needed by patients currently in the ED) is predicted to be high, this current impact can be utilized to predict the size of the influx of new patients before it occurs. Similarly, if the current impact on hospital resources is low, this factor can be used to predict that the size of the new patient influx will also be low. These assumptions are based on historical trends found in historical databases 204 (shown in FIG. 2). That is, if current resource demand is high, past trends indicate that a high influx of patients into the ED is imminent, and if current resource demand is low, past trends indicate that a lower influx of patients is imminent.

As depicted in block 312, the processor then utilizes the current patient backlog (from block 304), the sum of triage classification levels of all patients currently in the ED (from block 306), the current change in patient arrival rates (from block 308), and the predicted current impact on the hospital resources (from block 310) to predict a size of an imminent influx of arriving patients into the ED.

As depicted in block 314, the predicted size of the imminent influx of arriving patients is responded to and/or adjusted. For example, the processor can receive a notice of a non-recurring public event outside of the ED. An exemplary non-recurring public event may be the televised broadcast of a major sporting event. Logic within the processor "knows" that patients historically wait until such events are over to go to a hospital for treatment, or that many will be injured during post-event celebrations/disappointments. Based on this "knowledge" of such non-recurring public events, the processor adjusts the predicted size of the imminent influx of arriving patients accordingly.

Note that "imminent" is defined as occurring within a limited time period, which is not to exceed 24 hours. In one embodiment, "imminent" is defined as referring to patients arriving at the ED within the next two hours. In one embodiment, "imminent" is defined to describe the influx of patients who will arrive at the ED before an end of a current work shift in the hospital. In this embodiment, the processor responds to the predicted influx of patients by adjusting current staffing needs in the hospital in accordance with needs of the imminent influx of arriving patients.

The process ends at terminator block 316.

The flowchart and block diagrams in the figures illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of various embodiments of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Note further that any methods described in the present disclosure may be implemented through the use of a VHDL (VHSIC Hardware Description Language) program and a VHDL chip. VHDL is an exemplary design-entry language for Field Programmable Gate Arrays (FPGAs), Application Specific Integrated Circuits (ASICs), and other similar electronic devices. Thus, any software-implemented method described herein may be emulated by a hardware-based VHDL program, which is then applied to a VHDL chip, such as a FPGA.

Having thus described embodiments of the invention of the present application in detail and by reference to illustrative embodiments thereof, it will be apparent that modifications and variations are possible without departing from the scope of the invention defined in the appended claims.

What is claimed is:

1. A computer implemented method of dynamically predicting a size of an imminent influx of arriving patients into an emergency department of a hospital, the computer implemented method comprising:

a processor receiving an input that describes a quantity of current patients in each triage classification level, wherein the current patients are waiting in an emergency department on a current date;

the processor determining a longest wait time that a patient, from each triage classification level, is currently waiting in the emergency department;

the processor determining an average wait time that patients, from each triage classification level, are currently waiting in the emergency department;

the processor calculating a current patient backlog in the emergency department based on the quantity of current patients, the longest wait time for each triage classification level and the average wait time for each triage classification level;

the processor calculating a sum of weight-adjusted triage classification levels of all of the current patients waiting in the emergency department, wherein a larger sum of weight-adjusted triage classification levels of all patients currently in the emergency department predicts a relatively higher imminent influx of arriving patients into the emergency department, and wherein a smaller sum of weight-adjusted triage classification levels of all patients currently in the emergency department predicts a relatively lower imminent influx of arriving patients into the emergency department;

the processor tracking current patient arrival rates in the emergency department to calculate a current change in patient arrival rates; and the processor utilizing the current patient backlog, the sum of weight-adjusted triage classification levels of all patients currently in the emergency department, and the current change in patient arrival rates to predict a size of an imminent influx of arriving patients into the emergency department, wherein predicting the size of the imminent influx of arriving patients is performed by utilizing historical trends from a historical database, wherein the historical database contains data describing a previous patient backlog in the emergency department on a previous date, a sum of weight-adjusted triage classification levels of all patients previously in the emergency department on the previous date, and a previous change in patient arrival rates in the emergency department on the previous date.

2. The computer implemented method of claim 1, further comprising:

the processor comparing the current change in patient arrival rates to historical changes in patient arrival rates, wherein the historical changes in patient arrival rates are from one or more prior dates that share a common feature with the current date;

the processor determining a previous impact on hospital resources by patients from the emergency department, wherein the previous impact corresponded to the historical changes to patient arrival rates;

the processor utilizing the previous impact to create a predicted current impact on hospital resources, wherein the predicted current impact is for predicted use of the hospital resources by the current patients; and the processor utilizing the predicted current impact on the hospital resources to further predict the size of the imminent influx of arriving patients into the emergency department.

3. The computer implemented method of claim 2, wherein the common feature is a same holiday on which the current date and the prior dates fall.

4. The computer implemented method of claim 2, wherein the common feature is a same calendar date on which the current date and the prior dates fall.

5. The computer implemented method of claim 2, wherein the common feature is a same time of day of the current date and the prior dates.

6. The computer implemented of claim 1, further comprising:

the processor receiving a notice of a non-recurring public event, wherein the non-recurring public event occurs outside of a hospital, and wherein the emergency department is part of said hospital; and the processor adjusting a predicted size of the imminent influx of arriving patients to compensate for the non-recurring public event.

7. The computer implemented method of claim 1, wherein the imminent influx of arriving patients occurs within two hours.

8. The computer implemented method of claim 1, wherein the imminent influx of arriving patients occurs before an end of a current work shift in the hospital, and wherein the computer implemented method further comprises:

adjusting current staffing needs in the hospital in accordance with needs of the imminent influx of arriving patients.

9. The computer implemented method of claim 1, wherein each triage level has a unique triage weighting value, wherein the sum of weight-adjusted triage classification levels of all of the current patients waiting in the emergency department is calculated by adding all weighted patient triage values together, wherein each of the weighted patient triage values is calculated by multiplying each quantity of current patients at a particular triage level in the emergency department by the unique weighting value for the particular triage level.

10. A computer program product for dynamically predicting a size of an imminent influx of arriving patients into an emergency department of a hospital, the computer program product comprising:

a non-transitory computer readable storage media;

first program instructions to receive an input that describes a quantity of current patients in each triage classification level, wherein the current patients are waiting in an emergency department on a current date;

second program instructions to determine a longest wait time that a patient, from each triage classification level, is currently waiting in the emergency department;

third program instructions to determine an average wait time that patients, from each triage classification level, are currently waiting in the emergency department;

fourth program instructions to calculate a current patient backlog in the emergency department based on the quantity of current patients, the longest wait time for each triage classification level and the average wait time for each triage classification level;

fifth program instructions to calculate a sum of weight-adjusted triage classification levels of all of the current patients waiting in the emergency department, wherein each triage level has a unique triage weighting value, wherein the sum of weight-adjusted triage classification levels of all of the current patients waiting in the emergency department is calculated by adding all weighted patient triage values together, wherein each of the weighted patient triage values is calculated by multiplying each quantity of current patients at a particular triage level in the emergency department by the unique weighting value for the particular triage level;

sixth program instructions to track current patient arrival rates in the emergency department to calculate a current change in patient arrival rates;

seventh program instructions to compare the current change in patient arrival rates to historical changes in patient arrival rates, wherein the historical changes in patient arrival rates are from one or more prior dates that share a common feature with the current date;

eighth program instructions to determine a previous impact on hospital resources by patients from the emergency department, wherein the previous impact corresponded to the historical changes to patient arrival rates;

ninth program instructions to utilize the previous impact to create a predicted current impact on hospital resources, wherein the predicted current impact is for predicted use of the hospital resources by the current patients; and tenth program instructions to utilize the current patient backlog, the sum of weight-adjusted triage classification levels of all patients currently in the emergency department, the current change in patient arrival rates, and the predicted current impact on the hospital resources to predict a size of an imminent influx of arriving patients into the emergency department, wherein predicting the size of the imminent influx of arriving patients is performed by utilizing historical trends from a historical database, wherein the historical database contains data describing a previous patient backlog in the emergency department on a previous date, a sum of weight-adjusted triage classification levels of all patients previously in the emergency department on the previous date, and a previous change in patient arrival rates in the emergency department on the previous date; and wherein the first, second, third, fourth, fifth, sixth, seventh, eighth, ninth and tenth program instructions are stored on the non-transitory computer readable storage media.

11. The computer program product of claim 10, wherein a larger sum of weight-adjusted triage classification levels of all patients currently in the emergency department predicts a relatively higher imminent influx of arriving patients into the emergency department, and wherein a smaller sum of weight-adjusted triage classification levels of all patients currently in the emergency department predicts a relatively lower imminent influx of arriving patients into the emergency department.

12. The computer program product of claim 10, wherein the common feature is a same holiday on which the current date and the prior dates fall.

13. The computer program product of claim 10, further comprising:
    eleventh program instructions to receive notice of a non-recurring public event outside of the emergency department; and
    twelfth program instructions to adjust a predicted size of the imminent influx of arriving patients to compensate for the non-recurring public event; and wherein
    the eleventh and twelfth program instructions are stored on the non-transitory computer readable storage media.

14. The computer program product of claim 10, wherein the computer program instructions are downloaded to a client computer from a software deploying server in an on-demand basis.

15. A computer system comprising:
    a central processing unit (CPU), a computer readable memory, and a computer readable storage media;
    a computer readable storage media;
    first program instructions to receive an input that describes a quantity of current patients in each triage classification level, wherein the current patients are waiting in an emergency department in a hospital on a current date;
    second program instructions to determine a longest wait time that a patient, from each triage classification level, is currently waiting in the emergency department;
    third program instructions to determine an average wait time that patients, from each triage classification level, are currently waiting in the emergency department;
    fourth program instructions to calculate a current patient backlog in the emergency department based on the quantity of current patients, the longest wait time for each triage classification level and the average wait time for each triage classification level;
    fifth program instructions to calculate a sum of weight-adjusted triage classification levels of all of the current patients waiting in the emergency department, wherein a larger sum of weight-adjusted triage classification levels of all patients currently in the emergency department predicts a relatively higher imminent influx of arriving patients into the emergency department, and wherein a smaller sum of weight-adjusted triage classification levels of all patients currently in the emergency department predicts a relatively lower imminent influx of arriving patients into the emergency department;
    sixth program instructions to track current patient arrival rates in the emergency department to calculate a current change in patient arrival rates;
    seventh program instructions to compare the current change in patient arrival rates to historical changes in patient arrival rates, wherein the historical changes in patient arrival rates are from one or more prior dates that share a common feature with the current date;
    eighth program instructions to determine a previous impact on hospital resources by patients from the emergency department, wherein the previous impact corresponded to the historical changes to patient arrival rates;
    ninth program instructions to utilize the previous impact to create a predicted current impact on hospital resources, wherein the predicted current impact is for predicted use of the hospital resources by the current patients; and
    tenth program instructions to utilize the current patient backlog, the sum of weight-adjusted triage classification levels of all patients currently in the emergency department, the current change in patient arrival rates, and the predicted current impact on the hospital resources to predict a size of an imminent influx of arriving patients into the emergency department, wherein predicting the size of the imminent influx of arriving patients is performed by utilizing historical trends from a historical database, wherein the historical database contains data describing a previous patient backlog in the emergency department on a previous date, a sum of weight-adjusted triage classification levels of all patients previously in the emergency department on the previous date, and a previous change in patient arrival rates in the emergency department on the previous date; and wherein the first, second, third, fourth, fifth, sixth, seventh, eighth, ninth and tenth program instructions are stored on the computer readable storage media for execution by the CPU via the computer readable memory.

16. The system of claim 15, wherein the common feature is a same holiday on which the current date and the prior dates fall.

17. The system of claim 15, wherein the common feature is a same day of the week on which the current date and the prior dates fall.

18. The system of claim 15, further comprising:
    eleventh program instructions to receive notice of a non-recurring public event outside of the emergency department; and
    twelfth program instructions to adjust a predicted size of the imminent influx of arriving patients to compensate for the non-recurring public event; and wherein the eleventh and twelfth program instructions are stored on the computer readable storage media for execution by the CPU via the computer readable memory.

* * * * *